(12) United States Patent
Mahlin et al.

(10) Patent No.: US 8,308,762 B2
(45) Date of Patent: Nov. 13, 2012

(54) MEDICAL CLOSURE DEVICE

(75) Inventors: Fredrik Mahlin, Uppsala (SE); Fredrik Preinitz, Uppsala (SE)

(73) Assignee: St. Jude Medical Systems AB, Uppsala (SE)

( * ) Notice: Subject to any disclaimer, the term of this patent is extended or adjusted under 35 U.S.C. 154(b) by 123 days.

(21) Appl. No.: 12/921,993

(22) PCT Filed: Mar. 10, 2009

(86) PCT No.: PCT/IB2009/000478
§ 371 (c)(1),
(2), (4) Date: Sep. 10, 2010

(87) PCT Pub. No.: WO2009/112930
PCT Pub. Date: Sep. 17, 2009

(65) Prior Publication Data
US 2011/0029014 A1    Feb. 3, 2011

Related U.S. Application Data

(63) Continuation-in-part of application No. 12/076,246, filed on Mar. 14, 2008.

(51) Int. Cl.
*A61B 17/04* (2006.01)
(52) U.S. Cl. ........................ 606/215; 606/213
(58) Field of Classification Search ............ 606/215
See application file for complete search history.

(56) References Cited

U.S. PATENT DOCUMENTS

| | | | |
|---|---|---|---|
| 2,984,882 A | 5/1961 | Winn | |
| 5,282,827 A | 2/1994 | Kensey et al. | |
| 5,531,759 A | 7/1996 | Kensey et al. | |
| 5,593,422 A | 1/1997 | Muijs Van De Moer et al. | |
| 5,620,461 A | 4/1997 | Muijs Van De Moer et al. | |
| 5,830,234 A | 11/1998 | Wojciechowicz et al. | |
| 6,508,828 B1 | 1/2003 | Akerfeldt et al. | |
| 7,101,381 B2 | 9/2006 | Ford et al. | |
| 7,601,165 B2 * | 10/2009 | Stone | 606/232 |
| 7,658,751 B2 * | 2/2010 | Stone et al. | 606/232 |
| 7,717,929 B2 * | 5/2010 | Fallman | 606/158 |
| 8,109,965 B2 * | 2/2012 | Stone et al. | 606/232 |
| 2005/0137625 A1 | 6/2005 | Rissmann et al. | |
| 2006/0212072 A1 | 9/2006 | Cuevas et al. | |
| 2007/0049944 A1 * | 3/2007 | Stone et al. | 606/72 |
| 2007/0049970 A1 | 3/2007 | Belef et al. | |
| 2007/0239209 A1 * | 10/2007 | Fallman | 606/232 |
| 2008/0065114 A1 * | 3/2008 | Stone et al. | 606/139 |

(Continued)

OTHER PUBLICATIONS

U.S. Appl. No. 12/076,246, filed Mar. 14, 2008, Fredrik Mahlin et al.
Fredrik Mahlin et al., USPTO Office Action, U.S. Appl. No. 12/076,246, Oct. 4, 2010, 9 pages.
Fredrik Mahlin et al., USPTO Office Action, U.S. Appl. No. 12/076,246, Mar. 22, 2011, 12 pages.

(Continued)

*Primary Examiner* — Corrine M McDermott
*Assistant Examiner* — Todd J Scherbel
(74) *Attorney, Agent, or Firm* — Foley & Lardner LLP

(57) ABSTRACT

A medical closure device (1; 20) comprising an inner member (2; 23), which is adapted to be positioned against an inner surface of a tissue wall, and a retaining member (3; 13; 21), which is attached to the inner member, wherein the retaining member is in the form of a loop made up by multiple coils of at least one filament, the coils lying side-by-side one another such that when increasing tension is applied in the loop, at least one of the at least one filament breaks apart before side-by-side portions of the at least one filament slide readily with respect to one another.

11 Claims, 2 Drawing Sheets

U.S. PATENT DOCUMENTS

| | | | |
|---|---|---|---|
| 2008/0082128 A1* | 4/2008 | Stone | 606/232 |
| 2008/0208252 A1 | 8/2008 | Holmes | |
| 2009/0082805 A1* | 3/2009 | Kaiser et al. | 606/228 |
| 2009/0234377 A1 | 9/2009 | Mahlin et al. | |
| 2011/0106151 A1* | 5/2011 | McDevitt et al. | 606/228 |
| 2011/0106153 A1* | 5/2011 | Stone et al. | 606/228 |

OTHER PUBLICATIONS

USPTO Office Action, U.S. Appl. No. 12/076,246, Oct. 12, 2011, 20 pages.

USPTO Office Action, U.S. Appl. No. 12/076,246, Feb. 13, 2012, 16 pages.

* cited by examiner

MEDICAL CLOSURE DEVICE

CROSS-REFERENCE TO RELATED PATENT APPLICATIONS

This application claims priority to, and is a continuation-in-part of, U.S. patent application Ser. No. 12/076,246, filed Mar. 14, 2008. The entire contents of this Ser. No. 12/076,246 application is incorporated herein by reference for the devices and methods disclosed therein.

FIELD OF THE INVENTION

The present invention relates generally to the field of sealing or closure devices for, e.g., the sealing of a percutaneous puncture in a vessel wall, and in particular to the class of sealing devices that comprises an intra-arterial member, which is held in place by a retaining member, and more particular to the special characteristics of this retaining member.

BACKGROUND OF THE INVENTION

In U.S. Pat. No. 6,508,828, which is assigned to the present assignee and whose entire contents are incorporated herein by reference for the sealing devices and methods disclosed therein, a sealing device is disclosed for sealing a puncture hole in a vessel wall. This sealing device comprises an inner sealing member, an outer locking member, and a retaining member. The inner sealing member is adapted to be positioned at an inner surface of the vessel wall, while the outer member is adapted to be positioned at an outer surface of the vessel wall. In use, the inner and outer members sandwich the vessel wall, and are held together by the retaining member, to thereby seal the puncture hole in the vessel wall. Other examples of sealing devices that comprise an inner member and an outer member, which are held together by an elongated retaining member, can be found in, for example, U.S. Pat. Nos. 5,593,422 and 5,620,461. Other types of medical closure devices are described in U.S. Pat. Nos. 5,531,759 and 5,282,827, whose entire contents are incorporated herein by reference for the closure devices and methods disclosed therein. These devices have an inner member in the form of an anchor member and an outer member in the form of a plug.

The retaining member can be provided in the form of a loop, which has been made from a thread, suture, monofilament, multifilament, or some other thread-like structure, the ends of which have been joined together by means of a knot. As an alternative, the ends of the thread-like element can be glued together to thereby form a loop.

In the U.S. Patent Application Publications Nos. 2005/0137625 and 2007/0239209, whose entire contents are incorporated herein by reference for the sealing devices and methods disclosed therein, the drawbacks with knotting and gluing are discussed, and an alternative approach is presented, wherein the ends of, for example, a suture are joined together by embedding one portion of the suture within another portion of the same suture, such that as tension in the suture increases, the different suture portions are held together by the friction then acting between these suture portions.

The present invention is therefore directed to an improved method of joining an elongated, thread-like element into a loop suitable for holding at least an inner member being part of a sealing device in place, and a general object of the invention is to provide a sealing device comprising an inner member which is attached to a loop, which is manufactured by this improved method.

SUMMARY OF THE INVENTION

The above-mentioned object is achieved with a medical sealing device comprising an inner member which is attached to a retaining member described herein.

As was stated above, in a medical sealing or closure device it is generally known to hold an inner member thereof by means of a retaining member, which can be provided in the form of a suture or filament. The sealing device is usually delivered into a puncture hole by some kind of insertion and positioning assembly, and to arrange the retaining member in the form of a loop provides thereby certain advantages, because a loop can easily be attached to and handled by the other elements of the insertion and positioning assembly. For this reason it is less favorable to produce a loop from a thread whose ends are tied together, because there is a risk that the resulting knot gets stuck in the insertion and positioning assembly during the delivery procedure. To create a loop by gluing together the ends of a thread is also less practical, because, for example, glue has to harden, and care must be taken to ensure that there is no excess glue that can contaminate the other parts of the insertion and positioning assembly and thereby jeopardize its proper functioning. The most elegant way of creating a loop is perhaps to thread one portion of, for example, a suture into another portion of the same suture, such that when the suture is subjected to tension, friction between the suture portions increases and holds the loop intact. The threading of one portion of a suture into another portion of the suture is, however, a rather time-consuming procedure, and requires a considerable amount of manual dexterity to manufacture, and is less suited for large-scale production.

In contrast, the present invention introduces a novel technique for providing a retaining member in the form of a loop made from a thread-like structure. Herein the term "filament" will be used as a common term for all kinds of thread-like structures, including but not limited to threads, sutures, fibers, monofilaments, multifilaments, etc. According to one embodiment of the invention, a loop is created by winding up a single filament multiple times, to thereby create a knotless loop, which holds together purely due to the friction acting between the individual filament coils. It has been found that the winding preferably should be performed at least ten (10), and more preferably at least twenty (20) times, to thereby create a loop comprising at least ten and more preferably at least twenty turns or coils, all made up from the same filament.

In another embodiment of the invention, several individual filaments are (preferably simultaneously) wound multiple times into one common loop comprising several coils of each individual filament. In this embodiment, the preferred number of windings can be somewhat smaller, but at least five (5), and more preferably at least ten (10), windings should be performed, such that in the loop an individual filament is represented by at least five and more preferably by at least ten turns or coils. Another way of expressing this feature of a knotless loop according to the present invention is to say that in a cross-section of the loop there are at least five, and more preferably at least ten, smaller cross-sections present, which all originate from the same filament. The number of windings (coils) could, however, be much larger, and for a thin monofilament, the number of coils could exceed one hundred, or even be in excess of two or three hundred, depending on, in particular, the surface characteristics of the filament used.

To prevent any tendency of unwinding of the filament(s) in a loop, some adherent material or property can be provided to cause the filaments to adhere to one another. Such an adherent, which could be an adhesive or a tacky material, e.g. wax or grease, or a conventional suture coating material, can be applied either to the surface of the loop itself, or to the surface of the individual filaments constituting the loop. Herein, the term "adherent" is meant to encompass all such adherent materials. An adherent should, however, not be confused with an adhesive such as glue which is used as the actual means that holds the loop together. Herein, an adherent is mainly used to prevent the filaments of the loop from fraying, but such an adherent can also increase the friction between the surfaces of neighbouring filament coils in a loop.

In a particular embodiment of a loop according to the present invention, the loop can be provided with a thickened section created by winding at least one filament around a portion of the loop, i.e. this thickening winding is perpendicular to the coils making up the loop itself. Such a thickened section can, in a sealing device comprising an outer member, be used for friction locking of the outer member. A friction lock for an outer member is disclosed in, for example, the above-referenced U.S. Pat. No. 6,508,828, whose entire contents are incorporated herein by reference.

BRIEF DESCRIPTION OF THE DRAWINGS

FIG. 1b shows a cross-section taken at B-B of the loop member shown in FIG. 1a.

DETAILED DESCRIPTION OF THE PREFERRED EMBODIMENTS

For ease of understanding, embodiments of the present invention will be described with reference to a sealing device adapted for the sealing of a percutaneous puncture in a vessel wall, such as an artery wall. The invention could, however, be applied to other types of medical sealing or closure devices, for example devices for the closing of an opening or defect in a patient's heart (e.g. a so-called patent foramen ovale).

Figure 1A:
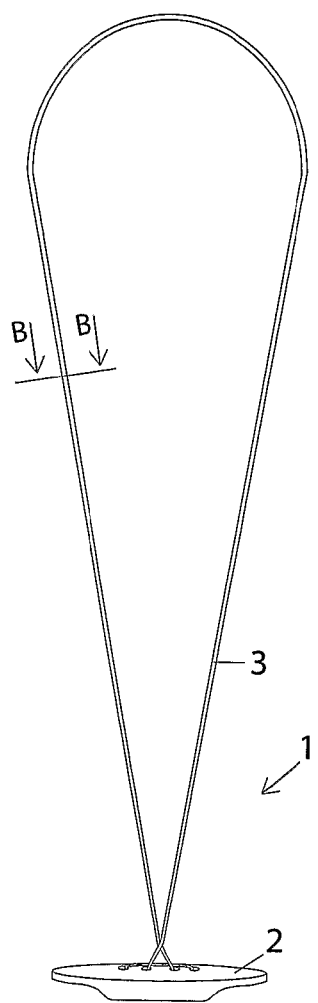
FIG. 1a illustrates schematically a sealing device comprising an inner member and a retaining loop member according to a first embodiment of the present invention.

In FIG. 1a, a first embodiment of a sealing device 1 comprising an inner member 2 and retaining member 3 in the form of a loop 3 according to the present invention is schematically illustrated. The inner member 2 is adapted to be introduced into a vessel (for example, a blood vessel) and positioned at an inner surface of the vessel wall, where the inner member 2 is held in place by tension applied in the retaining member 3. The retainer loop 3 has been created by winding up a thin filament multiple times such that the loop 3 has several coils of the same filament. Depending on in particular the surface characteristics of the filament used, the number of windings can easily be made sufficiently large such that a loop that holds together without the use of, for example, a knot or glue is produced. To prevent any tendency of the filament coils to fray, an adherent, like wax or suture coating, can be applied to the surface of the filament during winding. As an alternative, an adherent could be applied to the surface of the loop after the loop has been produced. Such an adherent can also enhance the friction characteristics of the filament surface, such that fewer turns are needed to create a loop that reliably holds together.

Figure 1B:
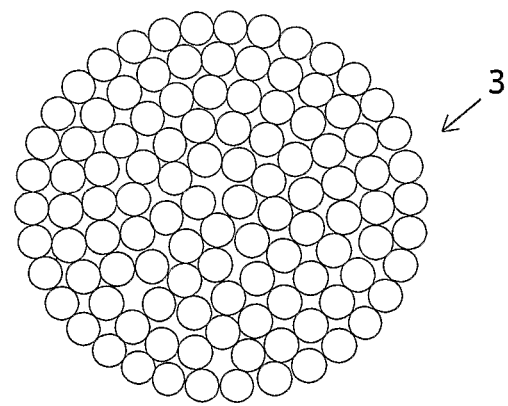

FIG. 1b illustrates very schematically a cross-section of the loop 3 shown in FIG. 1a. The cross-section of FIG. 1b, which is taken at B-B in FIG. 1a, is only intended to show that in a cross-section of a loop according to the first embodiment of the present invention, the same filament appears multiple times, in this case over hundred times. By providing multiple coils of the same filament, a loop which reliably holds together can thus be provided without using any knotting or gluing techniques.

Figure 2:
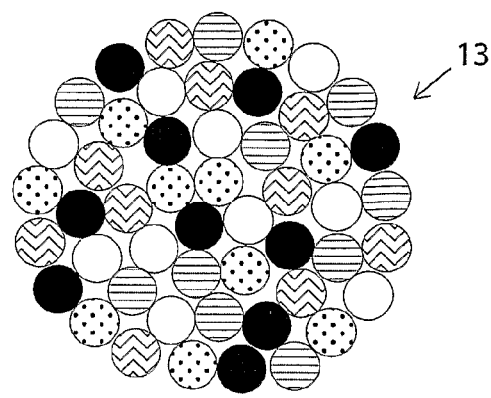
FIG. 2 shows a cross-section of an alternative retaining loop member according to a second embodiment of the present invention.

In FIG. 2 a cross-section of a second embodiment of a loop 13 according to the present invention is schematically illustrated. In this embodiment, several monofilaments have simultaneously been wound multiple times to create a composite loop 13. For illustrating purposes the number of monofilaments has been reduced to five (5), and the number of turns is ten (10), resulting in that each monofilament appears ten times in the cross-section and that the cross-section comprises a total of fifty (50) individual monofilament cross-sections. In practise, it may be preferred that these numbers, for example, are doubled, i.e. the number of monofilaments is ten (10) and the number of coils is twenty (20). It should, however, be emphasized that for a given situation, the adequate number of monofilaments as well as the adequate number of turns are very easily established by a few simple trials.

A similar way of manufacture a loop comprising multiple coils of the same filaments is to wind a multifilament multiple times. A multifilament consists of several filaments, which, for example, have been braided or twined into a multifilament. Also in this case, the result of the winding process is that a cross-section of the loop comprises several individual filament cross-sections, i.e. very similar to the cross-section shown in FIG. 2. In a test it was demonstrated that by winding a multifilament several times and thus providing a loop comprising several coils of the same filaments, the resulting loop would rather break than be drawn apart when large tension was applied. The test data is summarized in Table 1 below.

| Number of coils | Maximum tension applied to loop (Newton) just prior to failure | Mode of failure |
| --- | --- | --- |
| 2 | 4.3 | Sliding |
| 4 | 11.5 | Break |
| 8 | 33.5 | Break |
| 20 | 79.0 | Break |
| 30 | 108.1 | Break |

Table 1 shows the test results for a multifilament braided from twenty (20) filaments made from a segmented copolymer composed of L,L-lactide, trimethylene carbonate and ε-caprolactone with the weight percentage 88:8:4 and made by Poly-Med, Inc., South Carolina, U.S. The multifilament was wound into loops consisting of different numbers of coils. Each loop was then subjected to tension, and the maximum tension (in Newton) before failure as well as mode of failure were recorded. To prevent any unravelling tendencies of the loops, an adherent in the form of ordinary hair wax (Sportin' Waves® sold by Soft Sheen Products, Inc., Illinois, U.S.) was applied to the surface of the loops. As evident from Table 1, when the multifilament was wound only two (2) times, the mode of failure was sliding, whereas already four (4) windings produced a loop which instead broke. Herein, the failure mode "break" indicates that the filaments themselves break apart, while the failure mode "sliding" indicates that the filaments slide readily with respect to one another such that the loop unravels. The term "readily" is meant to distinguish this catastrophic unravelling of the filaments in a loop from a small and insignificant (initial) displacement or rearrangement of the filaments in a loop. Such a displacement or rearrangement can typically occur at the start of the tensioning of the loop in question.

The general purpose of a loop according to the invention is to function as a retaining member in a sealing device, wherein the retaining member holds an inner member. When the sealing device further comprises an outer member, which can slide along the retaining member until it is to be held in place by a friction lock created between the retaining member and a bore or hole in the outer member, a loop according to the invention can preferably be provided with a thickened portion. The inner member can be, for example, a seal or an anchor (sometimes called an anchor member or anchoring member). The outer member can be, for example, a seal, a locking device, or a plug. This thickened portion is advantageously also provided as a knotless portion in that one or several filaments are wound around a portion of a loop already created in accordance with the method described above. The windings of this thickened portion are thus directed perpendicular to the windings (or coils) of the basic loop. Alternatively, the transverse coils of a thickened portion can be made by winding of at least one filament which is not a continuous part of a filament forming the basic longitudinal loop.

Figure 3:
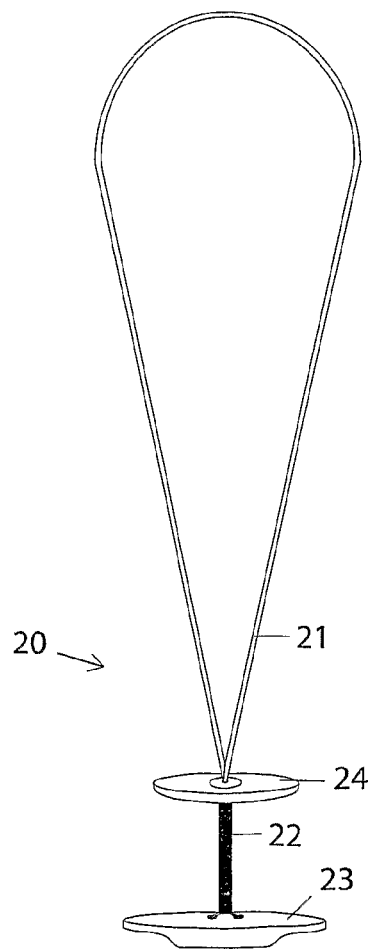
FIG. 3 illustrates a sealing device comprising an outer member, an inner member, and a retaining loop member according to another embodiment of the present invention.

Such a thickened portion is disclosed in FIG. 3, where a loop 21 is provided with a thickened portion 22 is schematically illustrated. A corresponding sealing device 20 can consequently comprise a retaining member 21 in the form of the loop 21 with the thickened portion 22, an inner member 23, which is connected to the retaining member 21, and an outer member 24, which is slidably attached to the retaining member 21 by a bore, which has been made through the outer member 24 and through which the loop 21 has been threaded. When the sealing device 20 is positioned at a vessel wall in order to stop bleeding through a puncture hole made therein, the inner member 23 is first positioned at an inner surface of the vessel wall, and then the outer member 24 is slid along the retaining member 21 until it is pushed up and over the thickened portion 22 into contact with an outer surface of the vessel wall, such that the inner member 23 and the outer member 24 sandwich the vessel wall and the outer member 24 is held in place by friction acting on the thickened portion 22 of the loop 21 and the bore made in the outer member 24, to thereby seal the puncture hole made in the vessel wall. As should be appreciated from FIG. 3, the thickened portion 22 has been created by multiple winding of at least one filament around a portion of the basic loop 21. The number of windings around the main loop 21 can easily be increased until the thickness of the thickened portion 22 is sufficiently large to reliably hold the outer member 24 in place.

As with the first embodiment of the invention shown in FIG. 1a and 1b, the loop 21 including the thickened portion 22 can be provided with an adherent, whose main purpose is to prevent any fraying tendencies of the filaments constituting the loop 21 and the thickened portion 22. Such an adherent can also enhance the friction acting between neighbouring filament coils in the loop, such that less coils are needed to provide a loop that reliably holds together.

Although the present invention has been described with reference to specific embodiments, also shown in the appended drawings, it will be apparent to those skilled in the art that many variations and modifications can be done within the scope of the invention as described in the specification and defined with reference to the claims below. It is in particular contemplated that the number of windings and thereby the number of resulting coils of a loop can range from a rather small number, e.g. five or ten, to a rather large number like several hundreds, depending on the specifics of the filament(s) used and the final strength required. A suitable number can easily be determined by a few simple experiments.

What is claimed is:

1. A medical closure device comprising:
   an inner member adapted to be positioned against an inner surface of a blood vessel having a puncture,
   an outer member adapted to be positioned against an outer surface of the blood vessel opposite the inner member, and
   a retaining member attached to the inner member and the outer member,
   wherein the retaining member is in a form of a loop comprising one or more filaments, each filament wound multiple times to form multiple coils of each filament, the coils lying side-by-side one another such that when increasing tension is applied in the loop, at least one of the one or more filaments breaks apart before side-by-side portions of the one or more filaments slide readily with respect to one another, and
   wherein the outer member is configured to perform one of locking the inner member to the puncture, sealing the puncture, and a combination thereof.

2. The medical closure device according to claim 1, wherein the retaining member is provided with a thickened portion made by a multiple winding of at least one filament around a circumference of a portion of the loop, and wherein the at least one filament forming the thickened portion is different from the one or more filaments forming the loop.

3. The medical closure device according to claim 1, wherein the loop is knotless.

4. The medical closure device according to claim 1, wherein the inner member is a seal.

5. The medical closure device according to claim 1, wherein the inner member is an anchor.

6. The medical closure device according to claim 5, wherein the outer member is in a form of a seal.

7. The medical closure device according to claim 1, wherein the outer member is a seal.

8. The medical closure device according to claim 7, wherein the inner member is a seal.

9. The medical closure device according to claim 1, wherein the outer member is a plug.

10. The medical closure device according to claim 1, wherein the inner member is an inner disc and the outer member is an outer disc.

11. The medical closure device according to claim 1, wherein the outer member is a plug of collagen foam.

* * * * *